United States Patent [19]

Steltenkamp et al.

[11] Patent Number: 4,682,982

[45] Date of Patent: Jul. 28, 1987

[54] ANTISTATIC N-HIGHER MONO ALKYL AND MONO ALKENYL NEOALKANAMIDES, PROCESSES FOR MANUFACTURING THEREOF, ANTISTATIC COMPOSITIONS CONTAINING SUCH AMIDES, AND PROCESSES FOR DECREASING ACCUMULATIONS OF STATIC CHARGES ON LAUNDRY

[75] Inventors: Robert J. Steltenkamp, Somerset; Michael A. Camara, Jackson, both of N.J.

[73] Assignee: Colgate-Palmolive Company, New York, N.Y.

[21] Appl. No.: 716,871

[22] Filed: Mar. 27, 1985

[51] Int. Cl.[4] .................... D06M 13/38; C07C 103/34

[52] U.S. Cl. .......................................... 8/137; 252/8.8; 252/525; 252/544; 260/404; 524/913; 564/138; 564/141

[58] Field of Search ........................ 252/8.8, 525, 544; 260/404; 564/138, 141; 524/913

[56] References Cited

U.S. PATENT DOCUMENTS

| | | | |
|---|---|---|---|
| 3,835,148 | 9/1974 | Oxe et al. | 524/913 |
| 3,843,543 | 10/1974 | Hewitt | 252/153 |
| 4,075,117 | 2/1978 | Morton et al. | 252/534 |
| 4,076,631 | 2/1978 | Caruso et al. | 252/8.8 |
| 4,418,011 | 11/1983 | Bauman et al. | 252/544 |
| 4,497,715 | 2/1985 | Bauman | 252/525 |

OTHER PUBLICATIONS

Mod et al., "N,N-Dialkylamides of Long Chain Fatty Acids as Plasticizers," J. Am. Oil Chemists' Soc. 42, (11), 941-44, (1965).

Fefer, "Neo Acids: Synthetic Highly Branched Organic Acids," J. Am. Oil Chemists' Soc., 55(4), 342A-345A, (1978).

*Primary Examiner*—Robert A. Wax

*Attorney, Agent, or Firm*—Herbert S. Sylvester; Murray M. Grill; Norman Blumenkopf

[57] ABSTRACT

N-higher alk(en)yl neoalkanamides are new compounds which unlike many other amides, are oily at washing temperatures, in the 10° to 90° C. range, and are capable of being adsorbed from wash and rinse waters by fibrous materials, such as laundry of synthetic, e.g., polyester, fabrics, which laundry is susceptible to being electrostatically charged, and decrease any electrostatic charge or inhibit accumulation thereof on such materials. Such neoalkanamides, e.g., N-coco-alkyl neodecanamide, can be incorporated in detergent compositions and in compositions for addition to laundry rinse waters, and in some instances it may be desirable for bentonite powder or agglomerate to also be included in such compositions to contribute fabric softening and other useful physical properties. Washing and rinsing operations are described in which N-higher alk(en)yl neoalkanamide is present in the waters, with and without supplementing small proportions of quaternary ammonium salt. Also described is a process for manufacturing higher alk(en)yl neoalkanamides in the form of oils which are desirably light in color and of improved purity.

19 Claims, 4 Drawing Figures

ANTISTATIC N-HIGHER MONO ALKYL AND MONO ALKENYL NEOALKANAMIDES, PROCESSES FOR MANUFACTURING THEREOF, ANTISTATIC COMPOSITIONS CONTAINING SUCH AMIDES, AND PROCESSES FOR DECREASING ACCUMULATIONS OF STATIC CHARGES ON LAUNDRY

This invention relates to novel alkanamides which have been found to be adsorbable from wash and rinse waters by fibrous materials, such as the fabrics of items of household laundry, especially synthetic polymeric fibers thereof, such as polyesters, and which have been found to impart to such fabrics antistatic properties, so that the accumulation or the development of electrostatic charges thereon is inhibited. More particularly, this invention is of: N-higher alkyl and N-higher alkenyl neoalkanamides of 5 to 16 carbon atoms in the acyl moieties thereof and 8 to 20 carbon atoms in the alkyl and/or alkenyl groups of the amine moieties thereof, such as neodecanamides, neopentanamides, neoheptanamides, neononanamides, neododecanamides, neotridecanamides and neotetradecanamides; method for their manufacture; detergent, rinse and other antistatic compositions and products containing them; and methods of treating laundry with such compositions in washing, rinsing and other operations to impart antistatic properties to it.

Neodecanoic and neopentanoic acids are presently being marketed by Exxon Chemical Americas and are described in a bulletin issued by such company and entitled Neo Acids Properties, Chemistry and Applications (copyright 1982). Other neoalkanoic acids have also been made, such as neoheptanoic acid, neononanoic acid and mixed neododecanoic, neotridecanoic and neotetradecanoic acids. Amides of neo acids and methods for their manufacture are referred to broadly at page 10, column 1 of such bulletin, and uses of various neoalkanamides including a neodecanamide (called a neodecanoamide in the bulletin are mentioned therein, including applications as pesticides, plasticizers (for polyvinyl chloride), foam boosters, foam suppressants, and slip agents (for polyolefin films). However, no mention is made of any of the neoalkanamides of the present invention and the preferred manufacturing method, which results in the production of light colored, better product, is not taught, nor are they suggested for use as antistats.

Computer searches of U.S. patents for the period 1950–1984 and of Chemical Abstracts for the period 1967–1985 have resulted in the finding of U.S. Pat. No. 4,440,666, directed to a hydrocarbon liquid containing a minor proportion of a reaction product of a polyalkylene polyamine and a neo-acid of 5 to 20 carbon atoms, in which the amide acts as a corrosion inhibitor. This patent does not appear to disclose any N-higher alkyl or alkenyl neoalkanamide and does not suggest that any such compounds would have antistatic properties. None of the other references found in the computer search discloses or suggests N-higher alkyl or alkenyl neoalkanamides, any antistatic properties of such or closely related compounds, or their inclusion in detergent, rinse or other laundry treating compositions, and none discloses or suggests applicants' process for manufacturing such amides of better color (and higher purity).

Because modern synthetic organic detergents are excellent cleaning agents and, unlike soaps, do not normally leave deposits of fatty materials on washed laundry, often laundry washed with them lacks desirable softness. Because synthetic polymeric fibers, which are the fibers of the fabrics of much of such laundry, are susceptible to disadvantageous accumulations of static charges, which occur during machine drying or when the fabrics are rubbed against other materials, with such tendency to static accumulation and resulting discharging or sparking being exacerbated by the absence of any fatty acid or insoluble soap coating on the fibers, much research has been conducted in an effort to discover materials which, when incorporated in detergent compositions or in rinse waters, would diminish any static charges on the laundry or would inhibit the accumulation of such charges.

Quaternary ammonium salts, such as di-lower alkyl di-higher alkyl ammonium halides, e.g., dimethyl distearyl ammonium chloride, have been used as fabric softeners in detergents, in fabric softening compositions for addition to the rinse water, and in papers, sponges and other substrates intended for introduction into laundry dryers, where they transfer such cationic materials to the laundry being tumbled. Certain amines have also been found to be useful in some such applications. However, because such cationic materials react objectionably with anionic detergents their use in anionic detergent compositions results in production of undesirable reaction products and causes losses of detergency.

It is an important feature of the present invention that certain amides have been discovered which are water insoluble and which may be in desired oily or plastic, flowable or spreadable state at normal use temperatures, e.g., 10° to 90° C., preferably 10° to 60° C. Particular amides which have the desired physical characteristics, are adsorbable or otherwise depositable onto laundry from the wash water or rinse water in a washing machine, or can be deposited onto drying laundry in the dryer, are higher amides of neoalkanoic acids. In accordance with the present invention such novel compounds are N-higher alkyl and alkenyl neoalkanamides of neoalkanoic acids, such as amides previously mentioned, the acid moieties of which have 5 to 16 carbon atoms and preferably contain from 7 to 14 carbon atoms. Although some branching of the hydrocarbyls is acceptable under certain circumstances, it is preferable that the alkyl and alkenyl groups be substantially or essentially linear, and more preferably, they will be linear. Among the more preferable of the neoalkanamide are those wherein the alkyl or alkenyl is higher, of 8 to 20 carbon atoms, often preferably 12 to 18 carbon atoms, such as may be derived from coconut oil, tallow or hydrogenated tallow, which for the higher alkyls are herein referred to as coco alkyl, tallow alkyl and hydrogenated tallow alkyl, respectively. It should be noted that in this usage "alkyl" may be inclusive of hydrocarbyl groups containing minor unsaturation, as in tallow alkyl, which contains a minor proportion of a monounsaturated $C_{18}H_{35}$ group. Also within the invention are: a process for the production of such N-higher alk(en)yl neoalkanamides; detergent compositions comprising N-higher alk(en)yl neoalkanamides; detergent compositions containing such a neoalkanamide and a fabric softening proportion of bentonite; rinse compositions containing both such constituents; a substrate material containing such a neoalkanamide, for use in a laundry dryer; and processes for treating laundry with the neoalkanamide during washing, rinsing and/or drying.

Neodecanoic acid, which is available commercially from Exxon Chemical Americas in prime and technical grades, is synthesized by reacting a branched nonene and carbon monoxide under high pressure at an elevated temperature in the presence of an aqueous acidic catalyst (Koch reaction). The general mechanism involved includes generation of a carbonium ion followed by complexation with carbon monoxide and the catalyst to form a "complex", which is subsequently hydrolyzed to generate the free acid. The formula of the free acid is:

$$R-\overset{\displaystyle R'}{\underset{\displaystyle R''}{C}}-COOH$$

wherein the number of carbon atoms in R+R'+R" is 8; about 31% of the neodecanoic acid is of a structure wherein R' and R" are both methyl and R is hexyl; 67% is of a formula wherein R' is methyl, R" is of a carbon atoms content greater than that of methyl and less than that of R, and R is of a carbon atoms content less than that of hexyl and greater than that of R"; and 2% is of a formula wherein R' and R" are both of a carbon atoms content greater than that of methyl and less than that of R, and R is of a carbon atoms content less than that of hexyl and greater than those of R' and R". The dissociation constant (Ka) of neodecanoic acid is $4.20\times10^{-6}$. Among other neoalkanoic acids that are available may be mentioned others in the 5 to 16 carbon atom content range, such as neopentanoic, neoheptanoic, neononanoic, neodecanoic, neododecanoic, neotridecanoic-and neotetradecanoic acids.

To make the neoalkanamides of this invention the neoalkanoic acid, such as neodecanoic acid, may be reacted directly with a higher alkyl- or alkenyl-amine, which is very preferably a linear primary amine, $R'''NH_2$, but also may include slightly branched alkyls having less than 10 or 20% of their carbon atoms contents in branch(es), e.g., as in 2-methyl heptadecane. The higher alkylamines and alkenylamines employed will normally be of a number of carbon atoms in the range of 8 to 20, often preferably 12 to 18, but may include compounds of more or fewer carbon atoms too, providing that the amides made possess the desired properties, as described herein. Among the more preferred of the amine starting materials are coco alkyl amine, tallow alkyl amine (which contains a minor portion of oleyl amine), and hydrogenated tallow alkyl amine. Such materials are available from vegetable and animal sources, and amides made from them have been found to be excellent antistats, which are compatible with anionic detergents. Also especially useful amine starting materials are oleyl amine and octyl amine.

The invented amides, which are of the formula:

$$R-\overset{\displaystyle R'}{\underset{\displaystyle R''}{C}}-CO\overset{H}{N}-R''',$$

for the neodecanamides, may be made by reacting a neoalkanoyl chloride with a higher alkyl or alkenyl amine, $R'''NH_2$, but a less costly synthesis is directly from the neoalkanoic acid by reacting it with such amine at an elevated temperature. The product of such reaction, unfortunately, is often very dark in color, which can make it unsuitable for incorporation in desirably white detergent compositions, which would be discolored by the presence of the amide. Applicants have found that by reacting the neoalkanoic acid with the higher alkyl or alkenyl amine, e.g., coco alkyl amine, at a suitable elevated temperature, preferably about 250° C. for the coco-neodecanamide, under an inert gas or nitrogen atmosphere, a nearly water white oily product results (the desired amide) which constitutes a first, upper phase, and may be readily separated from a second, lower phase, which includes by-products and any excess of reactants.

Normally, the reaction temperature for making the various neoalkanamides of this invention will be in the range of 180° to 320° C. and reaction times will be from 5 to 8 hours, with stirring being continued during the entire reaction. The melting points of the products will normally be low, so that the products will desirably be liquids at room temperature or at normal use temperatures. The melting points of the coco alkyl-, tallow alkyl- and hydrogenated tallow alkyl-neodecanamides are <0° C., 15°-17° C. and 45° to 49° C., respectively while those of the octyl, oleyl, palmityl and stearyl counterparts are <0° C., 5° to 6° C., 37° to 38° C. and 35° to 40° C., respectively. The refractive indices for the coco alkyl and octyl neodecanamides are 1.4626 and 1.4596, respectively. Melting point for the other neoalkanamides of 5 to 16 carbon atoms in the neoalkanoic acid will be in the <0° to 60° C. range and preferably the amides will be oily liquids at temperatures of 50° C. or less, and may be in solid state at about room temperature.

Although the described N-higher alkyl neodecanamides are the preferred embodiments of the present invention, other highly branched acids may also be employed for the manufacture of higher alkyl amide antistats. When neopentanoic acid is employed (it is of the formula $$CH_3-\overset{\displaystyle CH_3}{\underset{\displaystyle CH_3}{C}}-COOH),$$

for the manufacture of N-higher alkyl neopentanamides antistatic action is obtained but not to the extent realized for the higher alkyl neodecanamides. Normally the neoacid employed will be of 5 to 16, preferably 7 to 14 carbon atoms, and such acids are obtainable by the described process when highly branched $C_4$–$C_{15}$ or $C_6$–$C_{13}$ olefins are employed as starting materials in the Koch reaction.

N-Higher alk(en)yl neoalkanamides of the present invention may be employed to treat various fibrous materials, including polyesters, nylons, polyacrylates and acetates blends of some or all of such materials and blends of any of such materials with natural fibers, such as cotton, to lower the tendencies thereof to accumulate objectionable static charges. They may also be used to treat non-fibrous polymeric materials, such as video tapes and cassettes, camera film and photographs, movie film, sound recording tapes and cassettes, plastic sheets and molded (and otherwise formed) plastic items, such as items made from polyvinyl chloride (or polyvinyl chloride sheeting). In such treatments the amides may be applied directly or in suspension or solution, as liquids, pastes or sprays, to the surfaces of the items to be treated, in comparatively small proportions, normally with the proportion of amide to that of treated material being in the range of 0.0001 to 0.2%, by weight.

Although the present antistats may be applied directly or in suspension or solution to materials being treated to make them static-free it is usually highly preferable for them to be incorporated in other compositions that are used for different treatments of such materials. Thus, it is desirable for such antistats to be incorporable in detergent compositions so that the laundry washed with such compositions will not accumulate annoying static charges. Such compositions will comprise a detersive proportion of a synthetic organic detergent and a sufficient proportion of an N-higher alkyl neoalkanamide to be antistatic characteristic imparting to washed laundry.

The neoalkanamides of this invention are especially advantageous for use in detergent compositions of the anionic type because, unlike quaternary ammonium halides, they do not react adversely with anionic detergents. Thus, they do not form objectionable fatty reaction products which can deposit on and mar the appearance of washed laundry, and they do not cause a diminution in detersive activity of the detergent composition. Furthermore, they are effective antistats, being adsorbable onto washed laundry especially synthetic polymeric fibers thereof, during the washing process. In preferred detergent compositions of this invention the synthetic organic detergent will be of the sulfate and/or sulfonate type, normally including a higher aliphatic chain, such as a higher alkyl of 8 to 20 carbon atoms, in the lipophilic portion thereof. Preferably, such materials will be employed as water soluble salts, e.g., sodium salts. While the present neoalkanamides may be employed in nonionic detergent compositions or detergent compositions of various types, including amphoteric, ampholytic or zwitterionic detergents, preferably the detergent will be an anionic detergent and will usually be one or more of the following: linear higher alkylbenzene sulfonates; branched higher alkylbenzene sulfonates; higher fatty alcohol sulfates; olefin sulfonates; paraffin sulfonates; monoglyceride sulfates; fatty alcohol ethoxylate sulfates; higher fatty acid sulfoesters of isethionic acid; higher fatty acyl sarcosides; and acyl- and sulfo-amides of N-methyl taurine. In such detergents there will normally be present a higher aliphatic or alkyl group, which is preferably linear, and which will usually be of 8 to 20 carbon atoms, more preferably 12 to 18. When lower alkoxy chains are present, as in the mentioned ethoxylate sulfate, usually there will be from 3 to 30 ethoxies, preferably 3 to 10. Such detergents will normally be employed as sodium salts although other water soluble salts, such as potassium, ammonium and triethanolamine salts, may be used too, in certain circumstances.

For heavy duty laundering applications the detergent composition will usually contain a builder, to increase the detergency of the anionic detergent, especially in hard water. Among the various builders that may be utilized those of preference include: the polyphosphates, sodium tripolyphosphate and tetrasodium pyrophosphate; carbonates; bicarbonates; sesquicarbonates; silicates; sesquisilicates; citrates; nitrilotriacetates; and polyacetal carboxylates; all of which are water soluble salts, and the water softening zeolites, such as hydrated Zeolite A, which are water insoluble.

The proportion of the invented neoalkanamide in the detergent composition will be an antistatic characteristic imparting proportion (to washed laundry adsorbing the neoalkanamide during washing) and such will normally be in the range of about 1 to 20% of the detergent composition, by weight, preferably being 3 to 15% and more preferably being 5 to 12%, e.g., about 10%. When heavy loads of laundry are to be treated the content of neoalkanamide in the detergent composition will preferably be about 6 to 10% or more, often 7 to 10%.

In addition to the neodecanamide, detergent and builder, the invented detergent composition, even when in solid or particulate form, will also usually contain some moisture. The proportion of moisture will usually be in the range of 2 to 20%, preferably being 3 to 15% and more preferably about 5 to 12%, e.g., about 8%. The particulate material will desirably be in the form of spray dried detergent composition beads, with particle sizes in the range of No's. 10 to 140, preferably 10 to 100, U.S. Sieve Series. Other forms of the detergent composition may be made, including liquids, gels, pastes, bars and cakes, and the particulate compositions and the compositions in such other forms will also normally contain functional and aesthetic adjuvants, and may contain fillers. Such adjuvants and fillers will normally comprise the balances of the detergents. Among the adjuvants that may be employed are: fluorescent or optical brightening agents, such as stilbene brighteners; anti-redeposition agents, such as sodium carboxymethyl cellulose; soil release promoting polymers, such as Alkaril QCF; fabric softening agents, such as bentonite; anti-gelling agents (for use in the crutcher), such as citric acid and magnesium sulfate; colorants, such as ultramarine blue pigment and dyes; whitening agents, such as titanium dioxide; enzymes, such as mixed proteolytic and amylolytic enzymes; and perfumes. Among the fillers or bodying agents that are sometimes employed the most preferred is sodium sulfate, although sodium chloride has also been used. In liquid detergent compositions water, lower alcohols, glycols, co-solvents and anti-freeze additives may also be present.

The proportions of detergent, builder, N-higher alkyl neoalkanamide and moisture in the invented particulate antistatic detergent will normally be within the ranges of 5 to 35%, 10 to 85%, 1 to 20% and 2 to 20%, respectively. Preferred proportions are 8 to 30%, 25 to 70%, 3 to 15% and 3 to 15%, respectively, with more preferred proportions being 10 to 25%, 30 to 70%, 5 to 12% and 5 to 12%, respectively. The moisture content includes hydrate moisture that is removed by the standard moisture test, heating for an hour at 105° C., and such removed moisture is not included in the weights of the other composition components.

The detergent composition, when in particulate form, may be made by spray drying an aqueous crutcher mix of the various constituents thereof to free flowing bead form, utilizing well known spray drying equipment and following a standard spray drying procedure, in which a hot drying gas, which is the products of combustion of fuel oil or gas, passes concurrently or countercurrently, with respect to falling spray droplets of an aqueous crutcher mix, to produce the dried beads, which are removed from the bottom of the spray tower, and subsequently may be screened or otherwise classified to desired particle size range. The beads resulting are excellent detergents and are capable of having the antistat component thereof adsorbed by laundry to lower any tendency of laundry to accumulate static charges. However, even greater antistatic activity is observable when the neoalkanamide is not spray dried with the rest of the detergent composition but is sprayed onto or otherwise applied to the spray dried detergent composition particles, base beads or to a detergent composition made by mixing together particulate components thereof. In a preferred process the neoalkanamide is dissolved in the formula proportion of liquefiable nonionic detergent at elevated temperature (40°-50° C.) and the solution is sprayed onto and absorbed by porous spray dried builder beads. The mentioned improved antistatic results are also obtainable by addition of the neoalkanamide antistat to the wash water, with separate addition thereto of the detergent composition. For such and other uses the antistat may be made in a convenient powder form for use by being first mixed with a suitable carrier, such as Microcel (a synthetic calcium silicate powder), a filler, e.g., particulate sodium sulfate, or a softening agent, e.g., bentonite, or other suitable material. When liquid, gel or paste detergent compositions are made, wherein the proportion of solvent or liquid medium is different from the moisture content of the solid or particulate products, the proportions of detergent, antistat, builder, when present, and adjuvants, when present, will be adjusted accordingly, normally with the relative proportions thereof being maintained about the same as in the solid compositions. However, the proportion of the neoalkanamide antistat in such detergent compositions and in other antistatic preparations will be maintained such as to be capable of imparting antistatic properties to the material to be treated, when the composition is employed in appropriate manner. One of skill in the art will be able to modify the formulations so as to make products of greatest utility and satisfactory stability. Similarly, it is contemplated that the formula will be changed when it is desired to produce compositions useful in the rinse or in the dryer. Rinse compositions may sometimes contain only the invented neoalkanamide dissolved in a suitable solvent medium or dispersed in an aqueous liquid medium, preferably with the aid of a hydrotrope or other surface active component. The proportion of antistat will preferably be kept about the same as that for the antistatic detergent composition previously discussed, e.g., 5 to 12%, although less could be used because in the absence of the detergent and builder the antistat will usually be more substantive. For liquid preparations for use in the rinse water, the proportion of solvent or liquid will normally be from 30 to 90%, while any surface active material or hydrotrope content will usually be in the range of 0.1 to 5%. If quaternary ammonium halide is also present the proportion thereof will desirably be in the range of one part of the quaternary compound to ½ to 10 parts of neodecanamide antistat. Additionally, when a polyurethane or cellulose sponge strip or a textile paper substrate is impregnated with the antistat of this invention (usually with the weight percentage thereof being from 10 to 100% of the weight of the substrate), a fatty material, such as monoglyceride or diglyceride of higher fatty acids may be present too, to aid in the depositing of the neoalkanamide onto the surfaces of the fabric fibers. A suitable such material is coconut oil fatty acids diglyceride.

When the invented neoalkanamide antistat is applied to laundry during the washing or rinsing operation, by adsorption thereof onto the laundry in the wash water or the rinse, the concentration of the detergent composition or the rinse preparation in the wash water will be sufficient to impart antistatic properties to the washed laundry, e.g., laundry items of polyester or polyester cotton blend fabrics. Such an effective concentration will normally be in the range of 0.005 to 0.1% of N-higher alkyl neodecanamide and preferably such range will be 0.01 to 0.05%. The detergent composition or rinse composition concentration in the wash water will normally be in the range of 0.05 to 0.5%, preferably being 0.08 to 0.2%. The wash or rinse water will normally be at a temperature in the range of 10° to 90° C., e.g., 30° to 50° C., with the lower part of the 10° to 90° C. washing temperature range being typical of American home laundry practice and the upper part of that range being that employed in European practice, especially when perborate-containing detergent compositions are employed (rinse temperature will normally be in the lower part of such range for both). In American practice the normal washing temperature will be in the range of 20° to 60° C. and for "cold water washing" and rinsings such range is often from 20° to 40° C. (or lower for rinsing). The washing operation will normally take between five minutes and one hour, with rinsing taking from two minutes to twenty minutes of that time. The water employed may be soft or hard and hardnesses between 0 and 250 p.p.m. (mixed calcium and magnesium hardnesses, as calcium carbonate) may be encountered. Under such washing and/or rinsing conditions the invented neoalkanamides are sufficiently substantive to the laundry being washed, especially that of synthetic organic polymers, such as polyesters, to be adsorbed thereon in sufficient proportion to make the polymer antistatic, thereby diminishing any static charges that could otherwise accumulate on the polymer during a machine drying (tumbling) operation or as a result of frictional forces applied to the polymer surface, as by rubbing against other materials. When washed laundry is treated in the dryer with substrate materials onto which the invented neoalkanamide or a mixture thereof with quaternary ammonium salt has been deposited it is found that the dried laundry resulting is of a diminished tendency to accumulate static charges.

While any of the methods of application of the invented neoalkanamides to material to be treated may be employed, and good antistatic properties will be transmitted to the treated material, it is within the invention to utilize a plurality of such application operations, such as washing, rinsing and drying, some or all in the presence of the antistat. Also, laundry may be brushed or sprayed with the antistat in solution or dispersion, and other materials, such as carpeting, may be similarly treated. However, a significant advantage of the present products is in their compatibility with anionic detergents in detergent compositions and wash waters, wherein antistatic proportions of quaternary ammonium salts often have undesirable effects on the detersive action of the anionic detergents and cause objectionable reactions which often result in spotting with the reaction products of the laundry or other items being washed.

The infrared absorption spectra for several representative N-higher alk(en)yl neoalkanamides are shown in the drawing, in which.

The following examples illustrate but do not limit the invention. Unless otherwise indicated, in these examples, the specification and claims, all parts given are by weight and all temperatures are in °C.

EXAMPLE 1

181 Grams of Arman CD coco alkyl amine are reacted with 142 grams of neodecanoic acid (prime grade, 95.2% pure) in a one-liter, 3-necked glass flask fitted with a magnetic stirrer, a heating mantle, an ice condenser, a nitrogen inlet and a communicating nitrogen source (to blanket the reaction). Prior to the reaction the flask had been purged of air and a nitrogen atmosphere had been introduced, which was maintained during the atmospheric pressure reaction. The reaction was conducted at 300° C. (the reaction range is from 180°-320° C., for this and the other condensation reactions) and was monitored by observing the water collected from the condenser. After seven hours it was considered that the reaction was essentially complete (8 ml. of water had been collected), and the flask was removed from the heating mantle. After being allowed to stand at room temperature over a long weekend (about 90 hours) the contents were transferred to a one-liter separatory funnel, washed sequentially with (a) 50:44:6 water:ethanol:HCl solution, (b) 56:44 water:ethanol solution, (c) 5% aqueous NaOH, and (d) distilled water, until neutral. After completion of washing the excess water was drained off and the washed product was dried in a vacuum rotary evaporator, yielding 273 grams of product.

Figure 1:
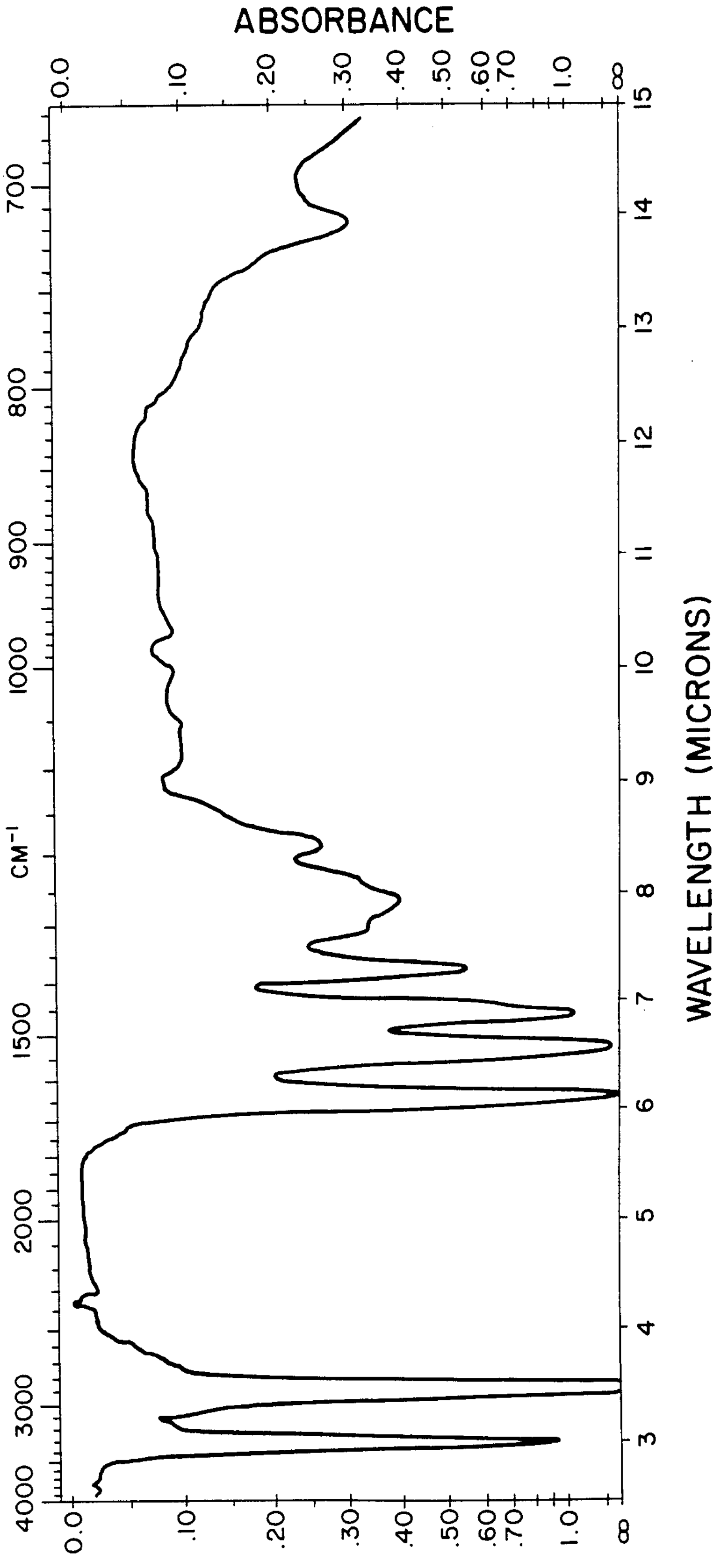
FIG. 1 is such an absorption spectrum for N-tallow alkyl neodecanamide.

The product is a light colored oil (Gardner No. 2), with a melting point less than 0° C. and a refractive index ($N_D$ 20° C.) of 1.4626. The infrared absorption spectrum for the N-coco alkyl neodecanamide made is given in FIG. 1. It will be noted that at about 3,350 $cm.^{-1}$ and 1,633 $cm.^{-1}$ strong absorption bands are present, indicating the presence in the compound of a secondary amide stretch (N-H) and a secondary amide carboxyl (C=O), respectively, and at 720 $cm.^{-1}$ there is a weak absorption band, indicating the presence of a long alkyl chain. The nuclear magnetic resonance spectrum was obtained and was found to be consistent with the expected structure. A peak in the proton spectrum for NH appears at 5.7 ppm.

When, instead of employing a nitrogen atmosphere over the reaction mixture there are used instead carbon dioxide, argon, or other gas inert to the reaction, or when vacuum is employed (preferably lower than 25 cm. of mercury), good, light colored product of essentially the same physical characteristics as previously mentioned results, in similar good yield. When vacuum is utilized it may often be desirable to lower the reaction temperature accordingly (usually about 10°-30° C.) to prevent possible losses of reactants and/or product. When a suitable inert gaseous atmosphere is not provided above the reactants, as when air is the gas that is present, the N-coco alkyl neodecanamide made is darker in color and may be unsuitable for incorporation in a retail detergent composition intended to impart antistatic properties to washed laundry.

An alternative reaction for the production of N-higher coco alkyl neodecanamide is the reaction of a gram-mole of a neodecanoyl chloride, which is slowly added over a period of about an hour to a gram-mole of coco alkyl amine dissolved in a solvent medium of 700 ml. of diethyl ether and a gram-mole of triethyl amine (which acts as a trap for HCl). The coco alkyl amine is in a 1-liter, 3-necked flask fitted with a condenser with a Drierite tube, a thermometer, a Chesapeake stirrer and a dropping funnel, and the flask is cooled by an ice bath.

After completion of addition of the neodecanoyl chloride the ice bath is removed and the reaction mix is allowed to come to room temperature, after which it is stirred for an additional hour. It is then transferred to a two-liter separatory funnel and is washed twice with water, once with 5% aqueous hydrochloric acid and once with 5% aqueous sodium hydroxide, followed by one or more washings with distilled water until the product is neutral to pH paper. Any remaining ether is removed by means of a steam bath and the product is finished on a vacuum rotary evaporator. The product made is water white to light amber in color, is pure, and exhibits the infrared and NMR spectra previously described for the same product made by the condensation method.

EXAMPLE 2

Figure 2:
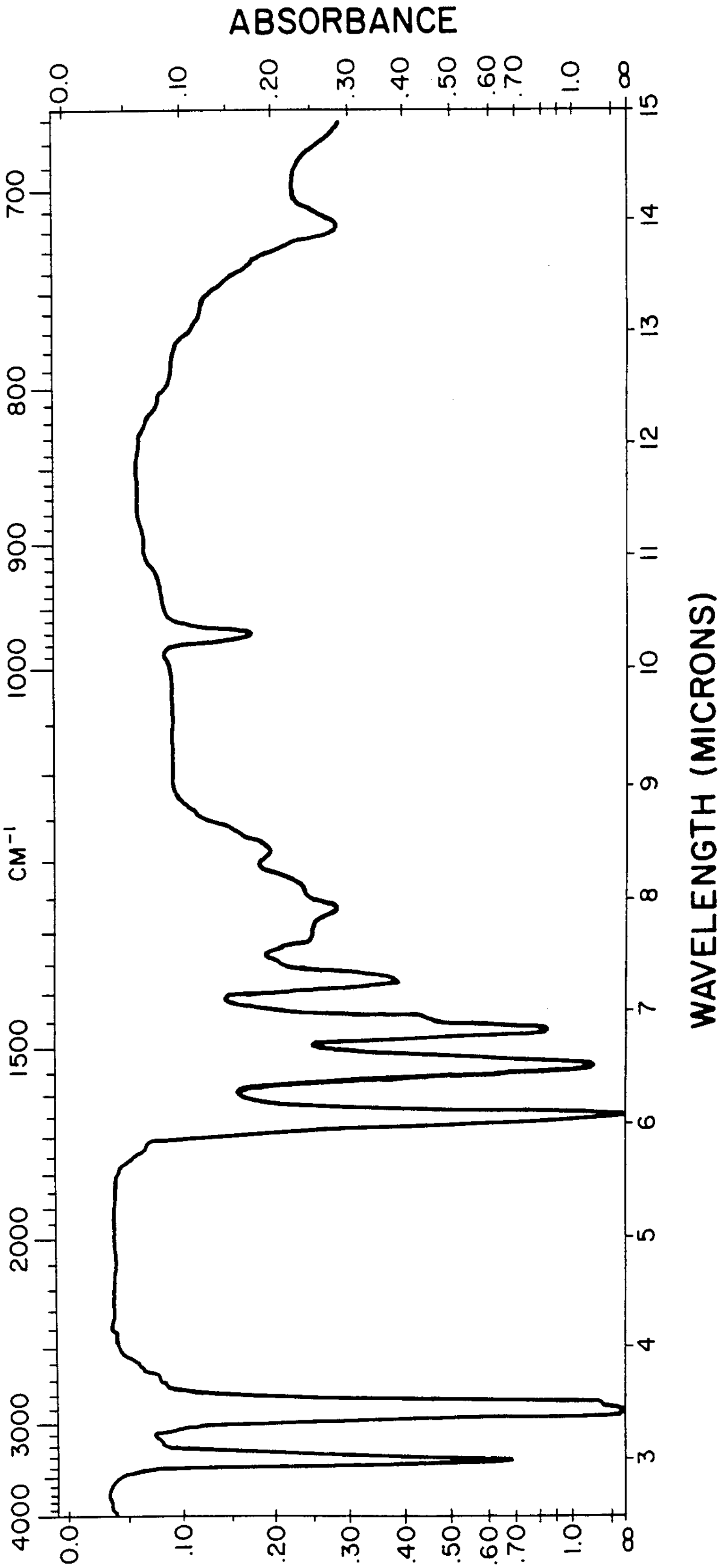
FIG. 2 is such a spectrum for N-coco alkyl neodecanamide.
Figure 3:
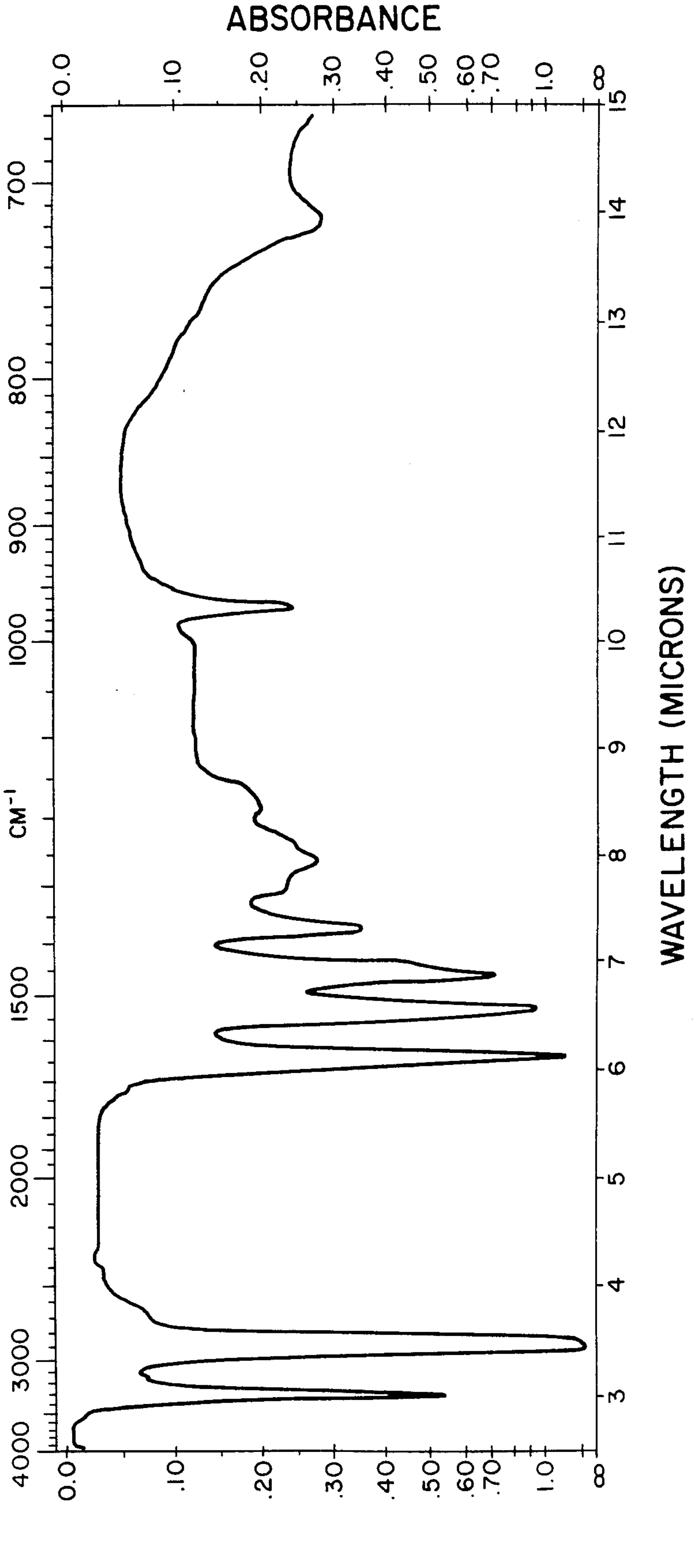
FIG. 3 is such a spectrum for N-hexadecyl neodecanamide.
Figure 4:
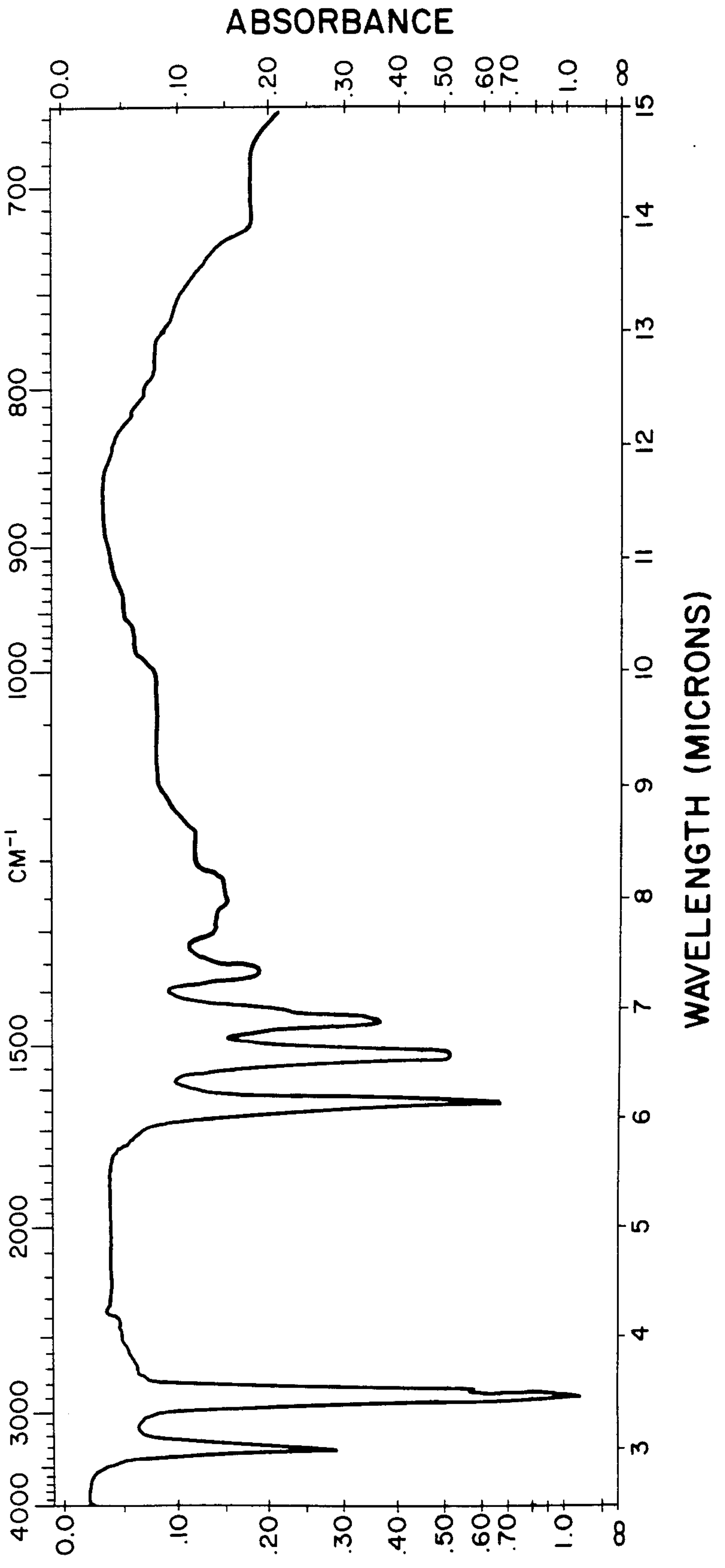
FIG. 4 is such a spectrum for N-oleyl neodecanamide.

Essentially the same procedure as that described in Example 1 is followed but the reactants are Armak tallow amine (199 g.) and neodecanoic acid (121 g., prime grade, 95.2% pure). The reaction was conducted under nitrogen over a period of about eight hours at a temperature in the range of 240°-260° C., and during that time eight ml. of water were collected. The washing solutions employed were the same as in Example 1 but four "final" washes with distilled water were made to produce a tallow alkyl neodecanamide that is neutral to pH paper. The final traces of water and alcohol were removed, utilizing a rotary evaporator. The yield was 159 grams of a light colored product (Gardner color=2) which included 2.5% of the starting amine and 0.3% of the starting acid. The tallow alkyl neodecanamide made has a melting point of 15°-17° C. and the infrared spectrum for it is illustrated in FIG. 2. As was described in Example 1, for the coco alkyl neodecanamide, the tallow alkyl neodecanamide can also be made by the acid chloride process, utilizing equal molar proportions of neodecanoic acid and tallow alkyl amine.

While the described condensation reaction, utilizing heating of the reactants in a flask under inert atmosphere, usually takes from 5 to 8 hours at a temperature in the range of 180° to 320° C. for the condensation process of this example and others herein given, longer reaction times, usually at lower temperatures, may be employed and shorter reaction times, sometimes at higher temperatures, may be utilized. A manufacturing apparatus for such quicker reactions may be a thin film reactor or comparable equipment.

EXAMPLE 3

N-tallow alkyl neopentanamide is made by reacting 51 grams of neopentanoic acid (obtained from Exxon Chemical Americas) with 134 grams of tallow amine-TD (obtained from Armak Chemical Company). The reaction is conducted in a 500 ml., 3-necked flask, equipped with a magnetic stirrer, a condenser with a Dean-Stark trap, and a nitrogen inlet, connected to a source of nitrogen. The flask was heated to 250° C. and after five hours the heat was turned off and the flask was allowed to set overnight. The product was transferred to a heated separatory funnel and was sequentially washed with aqueous alcoholic hydrochloric acid (53% water, 44% ethanol and 3% HCl), water-alcohol mixture (53% water, 47% ethanol), aqueous alcoholic sodium hydroxide (53% water, 44% ethanol and 3% sodium hydroxide) and distilled water (four washes), until the product was neutral to pH paper. The product made is of a melting point of 38° to 39° C.

EXAMPLE 4

The condensation reaction described in Examples 1–3 is also practiced to make N-methyl neodecanamide, N-ethyl neodecanamide, N-t-butyl neodecanamide, N-octyl neodecanamide, N-myristyl neodecanamide, N-hexadecyl neodecanamide (or N-palmityl neodecanamide), N-oleyl neodecanamide, N-hydrogenated tallow neodecanamide and N-stearyl neodecanamide. In all such reactions the apparatus employed is like that described in Examples 1–3, a nitrogen blanket is utilized, the time of reaction is from 5 to 8 hours and the reaction temperature is a suitable temperature in the range of 180° to 300° C. For the normally solid products the washings are conducted in a heated separatory funnel and heated washing agents are utilized.

The N-octyl neodecanamide and the N-oleyl neodecanamide are both oily materials, like the N-tallow alkyl neodecanamide and N-coco alkyl neodecanamide, and exhibit greater adsorptions onto fabrics or fibrous materials than do the other low melting neodecanamides made, which allows them to function more satisfactorily as antistats, useful for incorporation in detergent compositions to impart antistatic activity to washed laundry. The melting points of the products made are listed below in Table 1, together with the refractive indices for some that have melting points below 0° C.

TABLE 1

| Alk(en)yl (in N—alk(en)yl Neodecanamide | Melting Point (°C.) | Refractive Index ($N_D$ 20° C.) |
|---|---|---|
| Methyl | <0 | 1.4554 |
| Ethyl | <0 | 1.4554 |
| t-Butyl | <0 | |
| Octyl | <0 | 1.4596 |
| Myristyl | <0 | 1.4612 |
| Palmityl | 37–38 | |
| Oleyl | 5–6 | |
| Stearyl | 35–40 | |
| Hydrogenated tallow | 45–49 | |

In addition to varying the alk(en)yl group of the invented N-alk(en)yl neodecanamides within the 8 to 20 carbon range, as described in this example and in Examples 1 and 2, the neoalkanoic acid moiety of the present amides may also be changed. Thus, the condensation and acid chloride reactions of this example and Examples 1–3 may be practiced, with the substitution for the neodecanoic acid of this example and Examples 1 and 2 and for the neopentanoic acid of Example 3, of other neoalkanoic acids of carbon atoms contents in the range of 5 to 16, specifically neoheptanoic acid, neononanoic acid, neododecanoic acid, neotridecanoic acid and neotetradecanoic acid. The products within this invention that are made by the described reactions, especially the condensation reaction, as conducted under an inert gas atmosphere and with acidic, basic and distilled water washings of the product to pH neutrality, are amides with antistatic properties, which make them useful for the treatment of laundry to decrease or prevent static clinging thereof after machine drying. Especially preferred are the oily appearing amides, such as those wherein the alk(en)yl group is octyl, myristyl, oleyl or coco alkyl. However, the tallow alkyl neodecanamides and neopentanamides are also useful antistats and additionally possess fabric softening properties, especially when employed in conjunction with bentonite.

EXAMPLE 5

| Component | Percent |
|---|---|
| Sodium linear tridecylbenzene sulfonate | 13.4 |
| Sodium tripolyphosphate | 24.0 |
| Sodium silicate ($Na_2O:SiO_2$ = 1:2.4) | 6.3 |
| Sodium carbonate | 4.5 |
| Borax | 1.0 |
| Fluorescent brighteners | 0.3 |
| Methyl cellulose | 0.5 |
| Sodium carboxymethyl cellulose | 0.2 |
| Sodium sulfate | 49.6 |
| Perfume | 0.2 |
| | 100.0 |

A spray dried detergent composition of the above formula is made by spray drying an aqueous crutcher mix of 60% solids content in a conventional countercurrent spray drying tower to produce spray dried detergent beads, less perfume, which beads are subsequently perfumed by spraying onto the surfaces thereof the formula proportion of liquid perfume. The product is screened so that the particle sizes thereof will be in the range of No's. 10 to 100, U.S. Sieve Series. Then, desired proportions of oily neodecanamides, and N-tallow alkyl neopentanamide are sprayed onto the detergent composition beads to produce antistatic detergent compositions. Instead of mixing the neoalkanamide with the detergent composition to make an antistatic detergent composition, it may be added to the wash water, and sometimes is preferably added to the rinse. The effects of the antistat materials are evaluated by washing test fabrics in top loading Whirlpool washing machines and drying them in electric automatic clothes dryers, after which they are tested for static accumulations. A ballast load is employed in the washing machine with the test swatches and with soil removal index swatches, which are also present to check on any possible negative effect of the antistat on soil removal properties of the detergent composition. The ballast load (five lbs.) consists of ⅓ cotton terry face cloths; ⅓ cotton percale swatches (14″×15″); and ⅓ of 65% Dacron: 35% cotton swatches (14″×15″, without durable press finish). The test swatches used for antistatic effect measurement are 14″×15″ and include one each of: Dacron double knit twill; 65% Dacron: 35% cotton permanent press; blue 65% Dacron: 35% cotton permanent press; Banlon; acetate jersey; and nylon tricot. The soil removal index swatches measured 3″×6″ and four of each type are present with the ballast laundry. The five different types of such swatches are Test Fabrics Inc. soil on nylon, Test Fabrics Inc. soil on cotton; Piscataway (N.J.) clay on cotton; Piscataway clay on 65% Dacron: 35% cotton cloth; and EMPA 101 oily soil on 65% Dacron: 35% cotton cloth.

After thorough cleaning of the washers and dryers, using 3A denatured alcohol, followed by air drying, the washing machine is set for a 14 minute wash time, using 17 gallons of water at 120° F. This "hot" wash is one utilizing the normal machine cycle, including a cold rinse with tap water. The detergent composition, containing the antistat is added to the wash water after the machine is filled, the machine is allowed to agitate for about ten seconds and then the ballast load and the various test and soil removal index swatches are separately added, while agitation is continued. Subsequently the various fabrics are removed and placed in the electric dryer, where they are dried over a period of about two hours. The test swatches and two terry towels from the ballast are then dried for an additional ten minutes and the test swatches are then evaluated for static cling. Prior to instrumental static measurements the test swatches are hung in a low humidity room (25% relative humidity) overnight. The Blue 65 Dacron: 35 cotton swatch may be examined for product spotting and the reflectance (Rd) values of the soil removal index swatches may be determined, utilizing a reflectometer. Also, the cotton terry towels from the ballast may be evaluated for softness. To determine the static charges on the average test material, after washing with the detergent composition containing antistat, all of the static test swatches are rubbed in a controlled manner, with wool, under controlled conditions, at a relative humidity in the range of 25 to 30%, after which the electrostatic charges on the swatches are measured and the measured electrostatic charges are averaged for each material, after which the averages for the materials are again averaged, resulting in a static index. It has been found that differences of as little as 6 index units (in kilovolts) are significant and indicate that consumers will notice the difference in the static clings of washed materials different in static indices by six units.

The following table gives the static indices for detergent compositions of this example, which are charged to the washing machine at the rate of 100 grams per load (about 0.155%, on the basis of the wash water). The additional weights of neodecanamide employed (0 g., 3 g., 5 g., and 10 g.) are given in the table. The N-alk(en)yl neoalkanamides will be sprayed onto the detergent beads as liquids at room temperature or at elevated temperatures, but can be applied in solvents and may be mixed with the detergent as a powder, alone or with a carrier. In cases wherein multiple determinations were made, averages are given.

TABLE 2

| | 0 g./wash (control) [kilovolts] | 3 g./wash [kilovolts] | 5 g./wash [kilovolts] | 10 g./wash [kilovolts] |
|---|---|---|---|---|
| Alk(en)yl of N—alk(en)yl Neodecanamide | | | | |
| Methyl | 38 | — | — | 43 |
| Ethyl | 33 | — | 37 | 40 |
| t-butyl | — | — | — | 41 |
| Octyl | 41 | — | 26 | 7 |
| Coco alkyl (prime neodecanoic acid reactant) | 42 | 26 | 14 | 5 |
| Coco alkyl (technical neodecanoic acid reactant) | 45 | 19 | 11 | — |
| Myristyl | 31 | — | 11 | — |
| Palmityl | 43 | — | — | 26 |
| Tallow alkyl | 41 | — | 21 | 16 |
| Oleyl | — | 32 | 17 | 10 |
| Stearyl | — | — | — | 28 |
| Hydrogenated tallow alkyl | 46 | — | — | 32 |
| Alk(en)yl (of N—alk(en)yl neopentanamide) | | | | |
| Tallow alkyl | 46 | — | — | 20 |

When skilled evaluators of fabric properties examine the test fabrics washed with control and experimental detergent compositions for static cling they note no improvement for the N-methyl neodecanamide, N-ethyl neodecanamide and N-t-butyl neodecanamide but significant improvements are found for all the other neodecanamides reported in Table 2, at the various concentrations indicated.

Reflectometer readings of the soil removal index swatches showed no adverse effects on soil removal by the tested antistats. Similarly, the blue cloth was not adversely lightened in color, stained, or otherwise undesirably changed. in appearance, compared to a control.

When the other neoalkanamides described in this specification are tested in similar manner it will be found that they too impart desirable antistatic characteristics to washed laundry. Similarly, when other detergent compositions are utilized, such as non-phosphate detergent compositions containing zeolite builder, and nonionic detergent compositions, with or without phosphate builder and with or without zeolite builder, similar results are also obtainable. In addition to the particulate detergent compositions, liquid detergent compositions may also be employed, in which the neodecanamide may be dissolved and/or dispersed, or with which it may be added to the wash water in a washing machine. One such formula includes 16% of Neodol 25-7 (condensation product of one mole of higher fatty alcohol of 12 to 15 carbon atoms with 7 moles of ethylene oxide), 5.5% of denatured alcohol (3A), 3.1% of sodium linear dodecylbenzene sulfonate, 0.2% of fluorescent brightener, 3% of sodium formate, 1% (active ingredient basis) of soil release promoting agent (Alkaril QCJ), 0.8% of enzymes, 0.01% of blue dye, 0.4% of perfume, 10% of N-coco alkyl neodecanamide and 60% of water. It may also be desirable to incorporate about 5 to 10% of a hydrotrope, such as sodium benzene sulfonate, in the formula to stabilize it against settling out of the antistat.

EXAMPLE 6

Bentonite powder, of a fineness of about No. 200, U.S. Sieve Series, is agglomerated in known manner by tumbling it in an inclined drum while spraying onto falling curtains of the powder a relatively dilute aqueous sodium silicate solution (about 2%) until agglomerate beads of about the desired size result. Such beads are dried to acceptable moisture content, which may be about 11%. Thereafter the beads are screened to desired size range, such as No's. 10–60, U.S. Sieve Series. N-tallow alkyl neodecanamide, which is an oily liquid at room temperature, is sprayed onto the surfaces of the bentonite agglomerate beads while such beads are being tumbled in an inclined drum, and the porous bentonite beads absorb the neodecanamide so that the resulting particulate product remains free flowing. The proportion of neodecanamide in the product may be varied as desired but is desirably about 20%.

When one part of the N-tallow alkyl neodecanamide-bentonite agglomerate product is mixed with three parts of the detergent composition of Example 5 (that without neoalkanamide) the resulting composition contains 20% of bentonite and 5% of the neoalkanamide. Laundry washed with such composition, at a concentration in the wash water of about 0.2%, is noticeably soft (especially important for cotton items) and does not exhibit objectionable static cling (important for synthetic items). The laundry softening capability of the composition is greater than would have been attributed to the bentonite content thereof and it is considered that the N-tallow alkyl neodecanamide, in the presence of bentonite, either increases the bentonite softening activity or possesses independent softening characteristics. Similar bentonite-neoalkanamide products made with others of the described neoalkanamides do not exhibit the softening increasing effect obtained with the N-tallow alkyl neodecanamide but they are useful for their antistatic properties, in conjunction with the fabric softening activity of the bentonite.

Instead of spraying liquid state neoalkanamide onto the bentonite agglomerate it may be sprayed onto the finely divided powder before agglomeration, and may assist in agglomerating the bentonite. Also, for the neoalkanamides that are in solid state at room temperature mixtures of such in powdered form with bentonite powder may be made. Alternatively, such materials may be liquefied by means of heat or solvents, and may be applied to bentonite agglomerates or powders in such state.

Instead of employing the bentonite-neoalkanamide composition as an additive to a detergent composition to make it softening and antistatic, that composition may be used to treat already washed material, as in rinse water. The neoalkanamide, such as N-coco alkyl neodecanamide, N-myristyl neodecanamide, N-oleyl neodecanamide or N-octyl neodecanamide, may be added to either the wash water, rinse water or other aqueous treating medium in a sufficient concentration, normally in the range of 0.005 to 0.1%, to impart antistatic properties to fibrous materials. In such instances it will be normal to machine dry the fibrous material or laundry, as in a tumbling automatic laundry dryer. It is known that it is the act of drying the laundry while moving it which promotes the development of static charges thereon, which development is inhibited by treatment with a neoalkanamide of the present invention.

Although satisfactory antistatic action is obtained when the present neoalkanamides are employed in or with built laundry detergent compositions, and fabric softening is obtained from N-tallow alkyl neoalkanamide when it is employed with bentonite in or with detergent compositions, better antistatic action is noted and better softening effects for the neoalkanamides are obtained with tallow alkyl neodecanamide (with bentonite) when such are employed in rinsing steps, rather than in washing operations.

Wash cycle additive products of various types may be made, including particulate, paste, gel, liquid and solid tablet products, with the particulate material often preferably including inorganic builder salt, sodium sulfate, agglomerated bentonite and perfume, as well as neoalkanamide, which preferably is coco alkyl neodecanamide or tallow alkyl neodecanamide. One useful formula for such a particulate product includes: 66.8% of spray dried base beads made by spray drying, to a moisture content of about 8%, a crutcher mix containing 34.2 parts of water, 1.4 parts of fluorescent brightener, 1 part of magnesium sulfate monohydrate, 0.4 part of sodium polyacrylate, 32 parts of zeolite 4A, 2.5 parts of white montmorillonite (or bentonite), 17 parts of sodium bicarbonate (during which spray drying half of the sodium bicarbonate is converted to sodium carbonate), and 11.5 parts of soda ash; 21 parts of N-coco alkyl neodecanamide or N-tallow alkyl neodecanamide; 0.2 part of perfume; and 12 parts of agglomerated bentonite (10–60 mesh).

Instead of the base materials that have been recited for application of the neoalkanamide, other carriers may be employed, such as Microcel C (synthetic calcium silicate), sodium sulfate, soda ash or borax. Also, the neoalkanamide may be dissolved or dispersed in an aqueous, alcoholic or other suitable solvent medium and applied alone or with adjuvant(s). In some instances it may be desirable to spray a normally liquid state neoalkanamide onto surfaces to be made antistatic.

A liquid preparation for addition to the rinse water to render washed laundry antistatic may include about 91 parts of distilled water, about 1 part of perfume, about 0.3 part of nonionic detergent (preferably Neodol 25-7), about 2 parts of isopropanol and about 5.7 parts of N-coco alkyl neodecanamide, N-tallow alkyl neodecanamide or other suitable neoalkanamide within the invention.

EXAMPLE 7

A non-woven rayon sheet is impregnated with about 1.5 times its weight of coconut oil fatty acids diglyceride, about ½ its weight of N-coco alkyl neodecanamide (or N-tallow alkyl neodecanamide or other suitable neoalkanamide) and a desirable proportion (0.5%) of perfume. This product is useful as an antistatic sheet to be added to a laundry dryer, with the charge of sheeting to the dryer being such that about 10 grams of the neoalkanamide will be present therein for every five to 10 pounds of laundry (dry basis).

Alternatively, the neoalkanamide may be applied to the tumbling drying laundry by other mechanisms, including dispensing from a sponge or spraying or dripping liquid state neoalkanamide onto the tumbling laundry in the automatic dryer.

In the above description and examples it is to be understood that mixtures of the invented neoalkanamides may be employed, usually with the adjustment of the composition being such as to obtain most satisfactory antistatic action. Also, application conditions and proportions may be adjusted to obtain the desired results in the particular circumstances.

The invention has been described with respect to various embodiments and illustrations thereof but is not to be limited to these because it is evident that one of skill in the art will be able to utilize substitutes and equivalents without departing from the invention.

What is claimed is:

1. N-higher monoalkyl neoalkanamides or N-higher monoalkeynl neoalkanamides, or mixture thereof, wherein the alkyl and alkenyl groups are of numbers of carbon atoms in the range of 8 to 20 and the neoalkanoic acid moiety or moieties is/are of 5 to 16 carbon atoms.

2. N-higher monoalkyl neodecanamide according to claim 1 wherein the higher alkyl is of an average of 12 to 18 carbon atoms.

3. An N-higher monoalkyl neodecanamide according to claim 1 wherein the higher alkyl is linear.

4. An N-higher monoalkyl neodecanamide according to claim 3 wherein the higher alkyl is coco alkyl.

5. An N-higher monoalkyl neodecanamide according to claim 3 wherein the higher alkyl is tallow alkyl.

6. An N-higher monoalkyl neodecanamide according to claim 3 wherein the higher alkyl is hydrogenated tallow alkyl.

7. N-myristyl neodecanamide, according to claim 2.

8. N-palmityl neodecanamide, according to claim 2.

9. N-oleyl neodecanamide, according to claim 1.

10. N-tallow alkyl neopentanamide, according to claim 1.

11. A process for the production of N-higher neoalkanamide or N-higher monoalkenyl neoalkanamide, or a mixture thereof, as an oil which is light in color, which comprises reacting a higher alkyl amine or a higher alkenyl amine or a mixture thereof, wherein the higher alkyl or higher alkenyl or mixture thereof is of numbers of carbon atoms in the range of 8 to 20, with neoalkanoid acid of 5 to 16 carbon atoms at an elevated temperature, in the range of 180° to 320° C. under an inert gas or nitrogen atmosphere or under vacuum, and separating the product resulting from impurities, byproducts and unreacted amine and neoalkanoic acid.

12. A detergent composition comprising a detersive proportion of a synthetic organic detergent and a proportion, which is antistatic characteristic imparting to laundry during washing of N-higher monoalkyl neoalkanamide or N-higher monoalkenyl neoalkanamide or a mixture thereof, wherein the higher alkyl and higher alkenyl or mixture thereof are of numbers of carbon atoms in the range of 8 to 20, and the neoalkanoic moiety is of 5 to 16 carbon atoms.

13. A detergent composition according to claim 12 which is in particulate form and which comprises about 5 to 35% of synthetic organic detergent which is of sulfate type, sulfonate type or mixed sulfate and sulfonate types, about 10 to 85% of builder for such synthetic organic detergent, about 1 to 20% of N-higher monoalkyl neodecanamide wherein the higher alkyl is of a number of carbon atoms in the range of 8 to 20, about 2 to 20% of moisture, and the balance, if any, of filler, fillers, adjuvant, adjuvants, or a mixture of a filler or fillers with an adjuvant or adjuvants, with the particles of the detergent composition being in the No's. 10 to 140 range, U.S. Sieve Series.

14. A detergent composition according to claim 13 wherein the builder is selected from the group consisting of polyphosphates, carbonates, bicarbonates, sesquicarbonates, silicates, sesquisilicates, citrates, nitrilotriacetates, polyacetal carboxylates, zeolites, and mixtures thereof, the synthetic organic detergent is selected from the group consisting of linear higher alkylbenzene sulfonates, branched higher alkylbenzene sulfonates, higher fatty alcohol sulfates, olefin sulfonates, paraffin sulfonates, monoglyceride sulfates, higher fatty alcohol ethoxylate sulfates, higher fatty acid sulfoesters of isethionic acid, higher fatty acyl sarcosides, and acyl- and sulfo-amides of N-methyltaurine, the higher alkyl of the N-higher monoalkyl neodecanamide is of an average number of carbon atoms in the range of 12 to 18, and the proportion of N-higher monoalkyl neodecanamide in the detergent composition is from 7 to 10%.

15. A detergent composition according to claim 13 which is of improved fabric softening properties compared to such properties attributable to bentonite present, due to the presence of N-tallow alkyl neodecanamide therein, wherein the N-higher monoalkyl neodecanamide is N-tallow alkyl neodecanamide, which is in the detergent composition dispersed in a greater proportion of bentonite and mixed with other components of the detergent composition which are in spray dried bead form.

16. A process for washing laundry and simultaneously lowering its capacity to generate or hold an electrostatic charge, which comprises washing the laundry in an aqueous medium containing a detersive proportion of a detergent composition and an antistatic proportion of N-higher monoalkyl neoalkanamide antistat or N-higher monoalkenyl neoalkanamide antistat, or a mixture thereof, in which the higher alkyl and higher alkenyl are of numbers of carbon atoms in the range of 8 to 20, and the neoalkanoic moiety is of 5 to 16 carbon atoms, rinsing the laundry and drying it.

17. A process according to claim 16 wherein the detersive proportion of the detergent composition in the aqueous medium is from 0.05 to 0.5%, the antistat is N-higher monoalkyl neodecanamide wherein the higher alkyl is of a number of carbon atoms in the range of 8 to 20, and the antistatic proportion of such N-higher monoalkyl neodecanamide is in the range of 0.005 to 0.1%.

18. A process for treating laundry to lower its capacity to generate and hold an electrostatic charge which comprises washing the laundry in a wash water containing a detersive proportion of a detergent composition, and rinsing the laundry with rinse water containing an antistatic proportion of N-higher monoalkyl neoalkanamide antistat or N-higher monoalkenyl neoalkanamide antistat or a mixture thereof, wherein the N-higher alkyl and N-higher alkenyl are of numbers of carbon atoms in the range of 8 to 20 and the neoalkanoic moiety is of 5 to 16 carbon atoms, and drying the laundry.

19. A process according to claim 18 wherein the antistatic proportion of N-higher monoalkyl neodecanamide in the rinse water is in the range of 0.005 to 0.1%.

* * * * *